(12) United States Patent
Marraccini et al.

(10) Patent No.: US 7,148,399 B2
(45) Date of Patent: Dec. 12, 2006

(54) COFFEE MANNANASE

(75) Inventors: Pierre Marraccini, Savoniéres (FR); John Rogers, St. Genis Pouilly (FR); Raymond David Pridmore, Lausanne (CH); Christof Gysler, Blonay (CH)

(73) Assignee: Nestec S.A., Vevey (CH)

( * ) Notice: Subject to any disclaimer, the term of this patent is extended or adjusted under 35 U.S.C. 154(b) by 630 days.

(21) Appl. No.: 10/260,212

(22) Filed: Sep. 27, 2002

(65) Prior Publication Data

US 2003/0131380 A1 Jul. 10, 2003

Related U.S. Application Data

(63) Continuation of application No. PCT/EP01/01549, filed on Feb. 13, 2001.

(30) Foreign Application Priority Data

Mar. 30, 2000 (EP) .................... 00201175

(51) Int. Cl.
| | |
|---|---|
| C12N 15/29 | (2006.01) |
| C12N 15/52 | (2006.01) |
| C12N 15/56 | (2006.01) |
| C12N 15/82 | (2006.01) |
| A01H 5/00 | (2006.01) |
| A01H 5/10 | (2006.01) |

(52) U.S. Cl. ............ 800/284; 800/290; 800/298; 536/23.1; 536/23.2; 536/23.6; 435/320.1; 435/419

(58) Field of Classification Search .......... 800/278, 800/284, 290, 298; 536/23.1, 23.2, 23.6; 435/320.1, 419
See application file for complete search history.

(56) References Cited

U.S. PATENT DOCUMENTS

| 5,714,183 A | 2/1998 | Nicolas et al. ........... 426/45 |
| 5,874,269 A * | 2/1999 | Stiles et al. ............ 435/189 |

FOREIGN PATENT DOCUMENTS

| EP | 0 676 145 B1 | 10/1995 |
| WO | WO 95 06478 A | 3/1995 |
| WO | 97/20937 * | 6/1997 |
| WO | 99/24588 * | 5/1999 |
| WO | WO 92/24588 | 5/1999 |
| WO | WO 00/28046 | 5/2000 |

OTHER PUBLICATIONS

Bewley et al., XP002095786 Molecular cloning of a cDNA encoding a (1-4)-bets-mannan endihydrolase from the seeds of germinated tomator (*L. esculentum*), PLanta De Springer Verlan, vol. 203, pp. 454-459 (1997).

Giorgini et al, XP002098585, "Effect of embryo and exogenous GA3 ib ebdisoemuc ebdi-bets.-mannanase activity of Coffea arabica L. during germination and early seedling growth" Rev. Bras. Fiscol. Veg. Vol. 8, No. 1, pp. 43-49 (1999).

Alcala et al., XP002145173, "EST311336 tomato fruit red ripe, TAMU *Lycopersicon esculentum* cDNA clone cLEN19E21 5, mRNA sequence" EMBL Accession No. AW441940 (2000).

* cited by examiner

*Primary Examiner*—Russell P. Kallis
(74) *Attorney, Agent, or Firm*—Bell, Boyd & Lloyd LLC

(57) ABSTRACT

A DNA fragment derived from coffee encoding at least one enzyme involved in the hydrolysis of polysaccharides comprising pure or branched mannan molecules linked to each other via a β (1→4) linkage, and which has the the nucleic acid sequence SEQ ID NO.:1 or which is homologous to or hybridizes to a fragment of DNA having the nucleic acid sequence SEQ ID NO.:1.

10 Claims, 8 Drawing Sheets

FIGURE 1

```
              1                                                              50
Aspergillus   ---------- --MKLSHMLL SLASLGVATA LPRTPNHNAA TTAFPSTSGL
Trichoderma   ---------- -MMMLSKSLL SAATAASALA AVLQPVPRA. .SSFVTISGT
Lycopersicon  MSYARRSCI. ....CGLFLL FLALVCE... ...ANS.... ..GFIGVKDS
Mannanase1    MAFSRRSNIS NFSCCFLVII VLSLHCENHI VSSSAS.... ..RFIQTRGT
Mannanase2    MMSREKSLLL RCCSLSLALF ILLGVGEGHG EIASNSTSSS SFSFVKTRGT 51                                                             100
Aspergillus   HFTIDGKTGY FAGTNSYWIG FL....TNND DVDLVMSQLA ASDLKILRVW
Trichoderma   QFNIDGKVGY FAGTNCYWCS FL....TNHA DVDSTFSHIS SSGLKVVRVW
Lycopersicon  HFELNGSPFL FNGFNSYWLM HVAADPTERY KVTEVLKDAS VAGLSVCRTW
Mannanase1    RFVLGGYPFF FNGFNSYWMM HVAAEPSERH KISNVFREAA ATGLTVCRTW
Mannanase2    EFVMNGRPLY LNGFNAYWLM YMASDPSTRT KVSTTFQQAS KYGMNAARTW 101                                                            150
Aspergillus   GFNDVNTKPT DGTVWYQ.LH ANGTSTINTG ADGLQRLDYV VTSAEKYGVK
Trichoderma   GFNDVNTQPS PGQIWFQKLS ATG.STINTG ADGLQTLDYV VQSAEQHNLK
Lycopersicon  AFSDGGDR.. .......... ALQISPGIYD ERVFQGLDFV IAEAKKY...
Mannanase1    AFSDGGDR.. .......... ALQMSPGVYD ERVFQALDFV VSEARKYGVH
Mannanase2    AFSDGGYR.. .......... ALQQSPGSYN EDMFKGLDFV VSEAKKYGIH 151                                                            200
Aspergillus   LIINFVNEWT DYGGMQAYVT ...AYGA..A AQTDFYTNTA IQAAYKNYIK
Trichoderma   LIIPFVNNWS DYGGINAYVN ...AFGG..N A.TTWYTNTA AQTQYRKYVQ
Lycopersicon  .......... .......... .....GAQIS NDDEFYTHPM LKKYLKNHIE
Mannanase1    LILSLTNNYK DFGGRTQYVT WAKNAGVQVN SDDDFYTKNA VKGYYKNHIK
Mannanase2    LILTLVNNWE GYGGKKQYVQ WARDQGHYLN NDDDFFTDPI VRGYFKNHIK 201                                                            250
Aspergillus   AVVSR..... ...YSSSAAI FAWELANEPR CQ.GCDTSVL YNWISDTSKY
Trichoderma   AVVSR..... ...YANSTAI FAWELGNEPR CN.GCSTDVI VQWATSVSQY
Lycopersicon  KVVTRLNSIT KVAYKDDPTI MAWELMNEPR DQADYSGKTV NGWVQEMASF
Mannanase1    KVLTRINTIS RVAYKDDPTV MAWELINEPR CQVDFSGKTL NAWVQEMATY
Mannanase2    TVLTRINSIT GLAYKDDPTI FAWELMNEPR CQSDLSGKAI QDWISEMATH 251                                                            300
Aspergillus   IKSLDSKHLV TIGDEGF.GL DVDSDGSYPY TYGEGLNFTK NLGISTIDFG
Trichoderma   VKSLDSNHLV TLGDEGL.GL ST.GDGAYPY TYGEGTDFAK NVQIKSLDFG
Lycopersicon  VKSLDNKHLL.EVGMEGFYGD SIPERKSVNP GYQVGTDFIS NHLINEIDFA
Mannanase1    VKSLDNKHLL EIGMEGFYGD SMPGKKQYNP GYQVGTDFIT NNLIKEIDFA
Mannanase2    VKSIDSDHLL DIGLEGFYGE SVPQKKEYNP GYQVGTDFIS NNRIVQVDFA
```

FIGURE 1 Continued

```
             301                                                       350
Aspergillus  TLHLYPDSW. .....GTSYD WGNGWITAHA AACKAV.GKP CLLEEYGVTS
Trichoderma  TFHLYPDSW. .....GTNYT WGNGWIQTHA AACLAA.GKP CVFEEYGAQQ
Lycopersicon TIHAYTDQWV SGQSDDAQLV WMEKWITSHW EDARNILKKP LVLAEFGKSS
Mannanase1   TIHAYPDIWL SGQSDGAQMM FMRRWMTSES TDSKTILKKP LVLAEFGKSS
Mannanase2   TIHLYPDQWV PNSNDETQAQ FVDRWIKEHI DDSKYLLEKP LLLTEFGKSS 351                                                       400
Aspergillus  NHCAVESPWQ QT........ ....AGNATG ..ISGDLYWQ YGTTFSWG.Q
Trichoderma  NPCTNEAPWQ TT........ ....SLTTRG ..MGGDMFWQ WGDTFANGAQ
Lycopersicon RGQG....SR DIFMSSVYRN VYNLA..KEG GTMAGSLVWQ ...LMAHGME
Mannanase1   KDPGYSLYAR ESFMAAIYGD IYRFA..RRG G.IAGGLVWQ ...ILAEGMQ
Mannanase2   RSPGYQVAKR DAYLSHIYDT IYACAATRGG GVCGGNLFWQ ...VMAPGME 401                                                       450
Aspergillus  SPNDGNTFYY NTSDFTC.LV TDHVAAINAQ SK--------  ----------
Trichoderma  SNSDPYTVWY NSSNWQC.LV KNHVDAINGG TTTPPPVSST TTTSSRTSST
Lycopersicon NYDDGYCIVL GQTPSTTQII SDQAHVMTAL AR.SLN----  ----------
Mannanase1   PYADGYEIVL SQNPSTGRII SQQSRQMTSL DHMSSNRTNS QSNKLRNSKE
Mannanase2   SWGDGYEIVL EENPSTVGVI AQQSNRLSSL T---------  ----------

451                                                       494
Aspergillus  ---------- ---------- ---------- ---------- ----
Trichoderma  PPPPGGSCSP LYGQCGGSGY TGPTCCAQGT CIYSNYWYSQ CLNT
Lycopersicon ---------- ---------- ---------- ---------- ----
Mannanase1   Q--------- ---------- ---------- ---------- ----
Mannanase2   ---------- ---------- ---------- ---------- ----
```

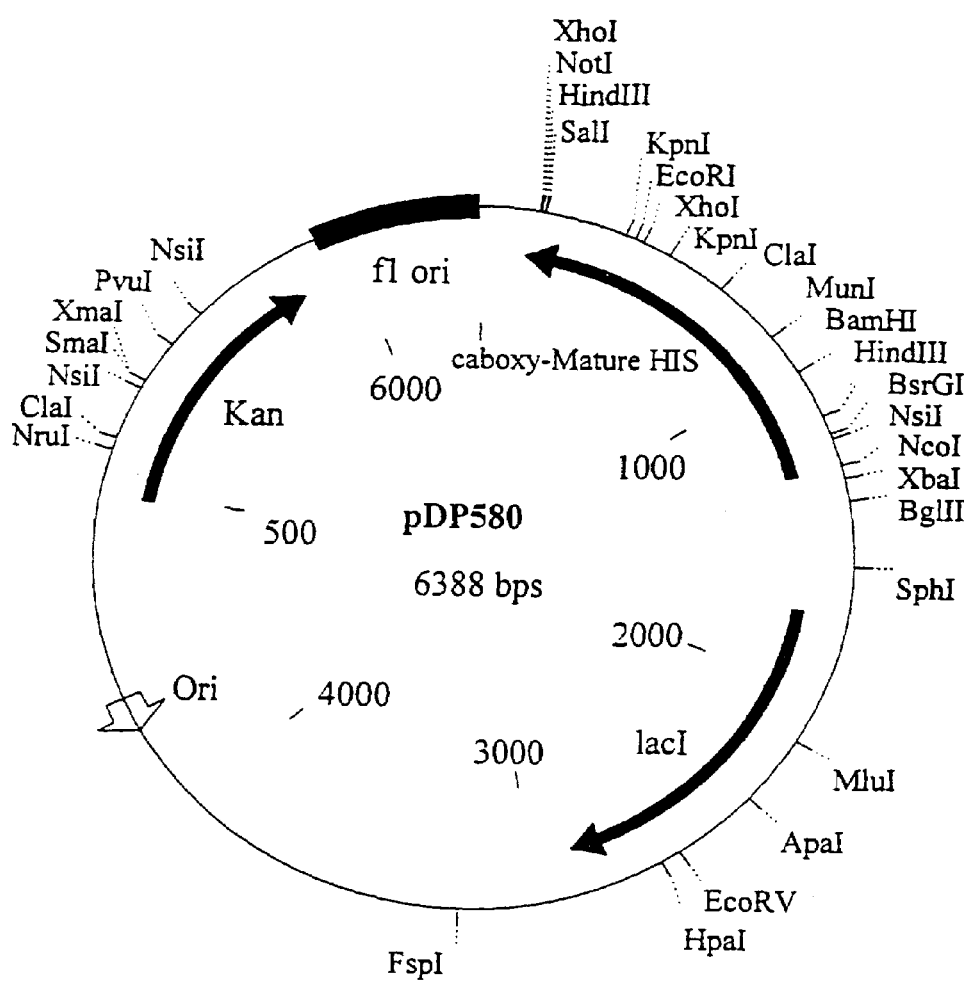
FIGURE 3. Physical map of plasmid pDP580.

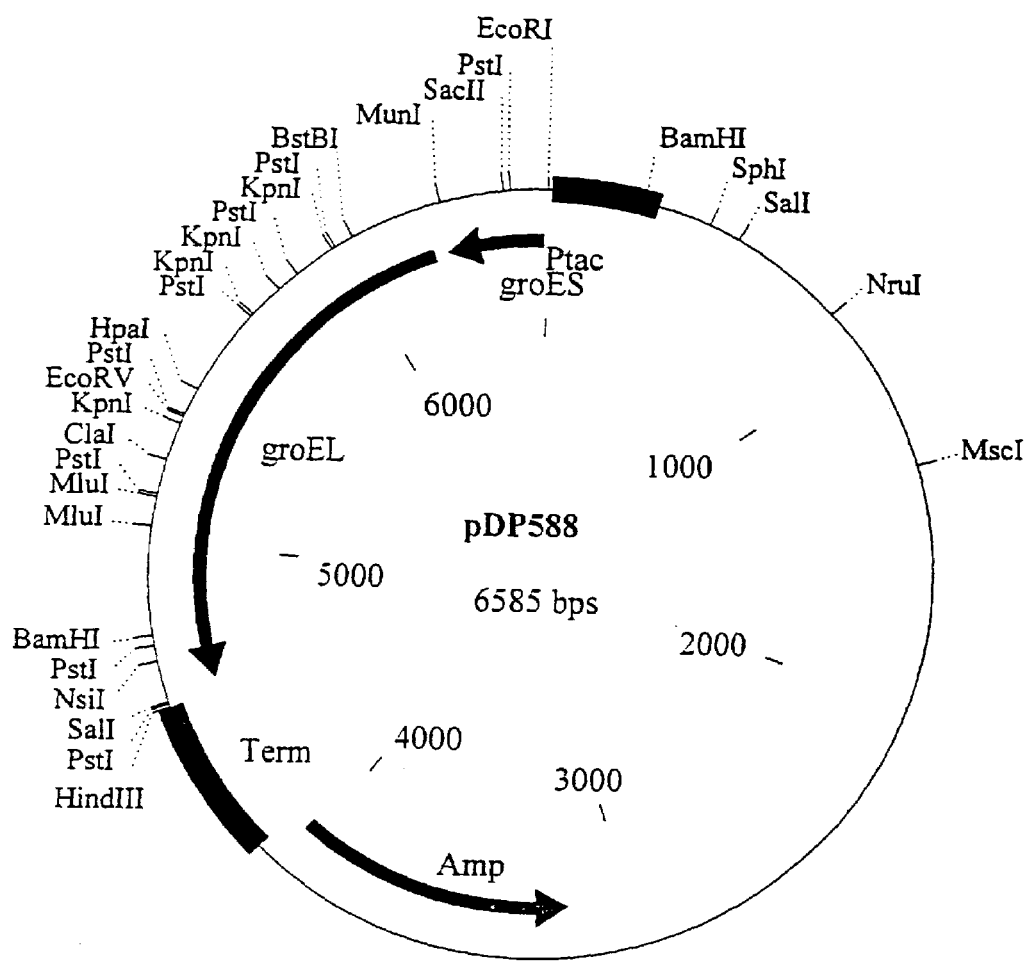
FIGURE 4. Physical map of plasmid pDP588.

FIGURE 5. Analysis by SDS-PAGE of IPTG-induced ManB expression in *E. coli* transformed with the plasmids pDP580 [carboxy HIS tag, mature ManB] (A) or pDP580 + pDP588 [for *groESL* expression] (B).
(+): indicates IPTG induction
(-): indicates control
supernatant B = water soluble fraction
pellet B = water insoluble fraction
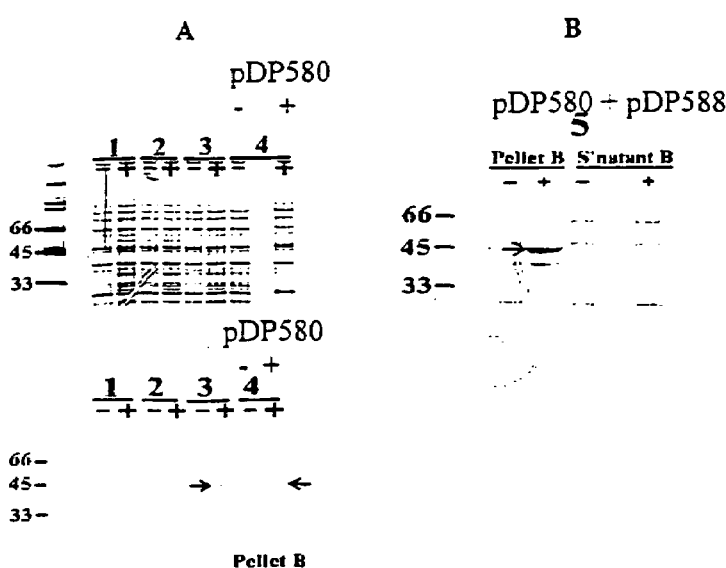

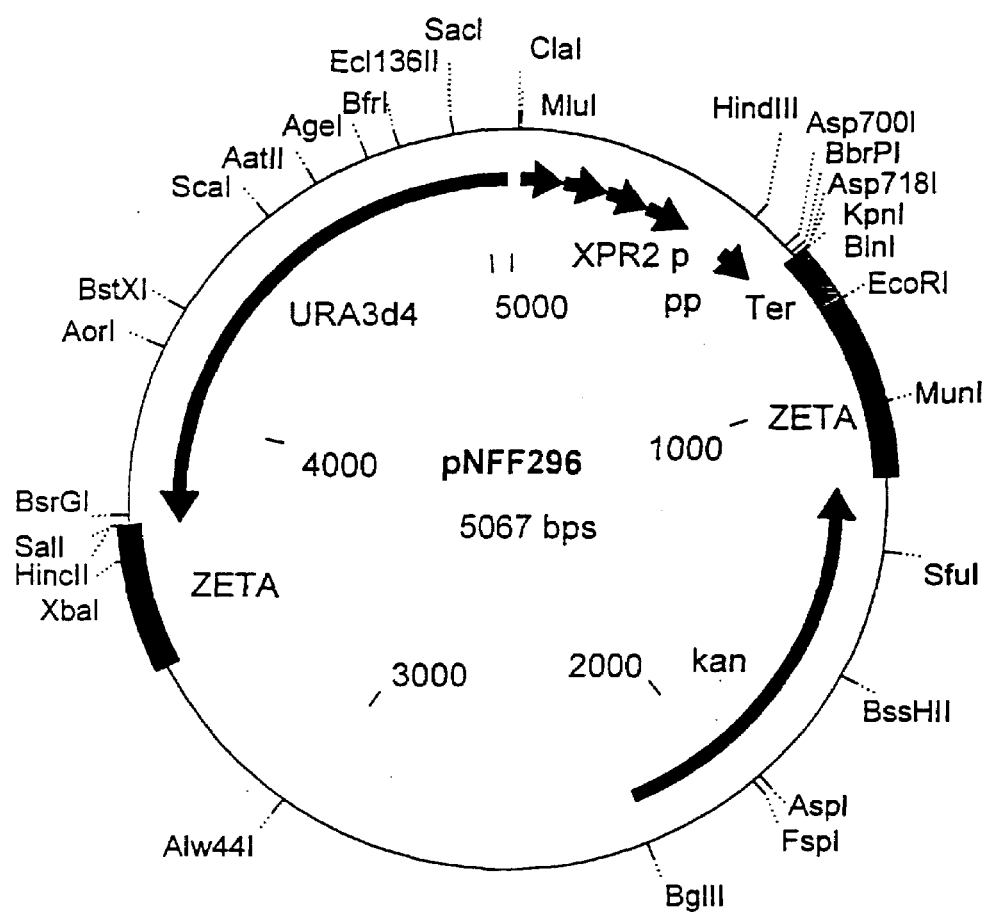
FIGURE 6: Physical map of plasmid pNFF296

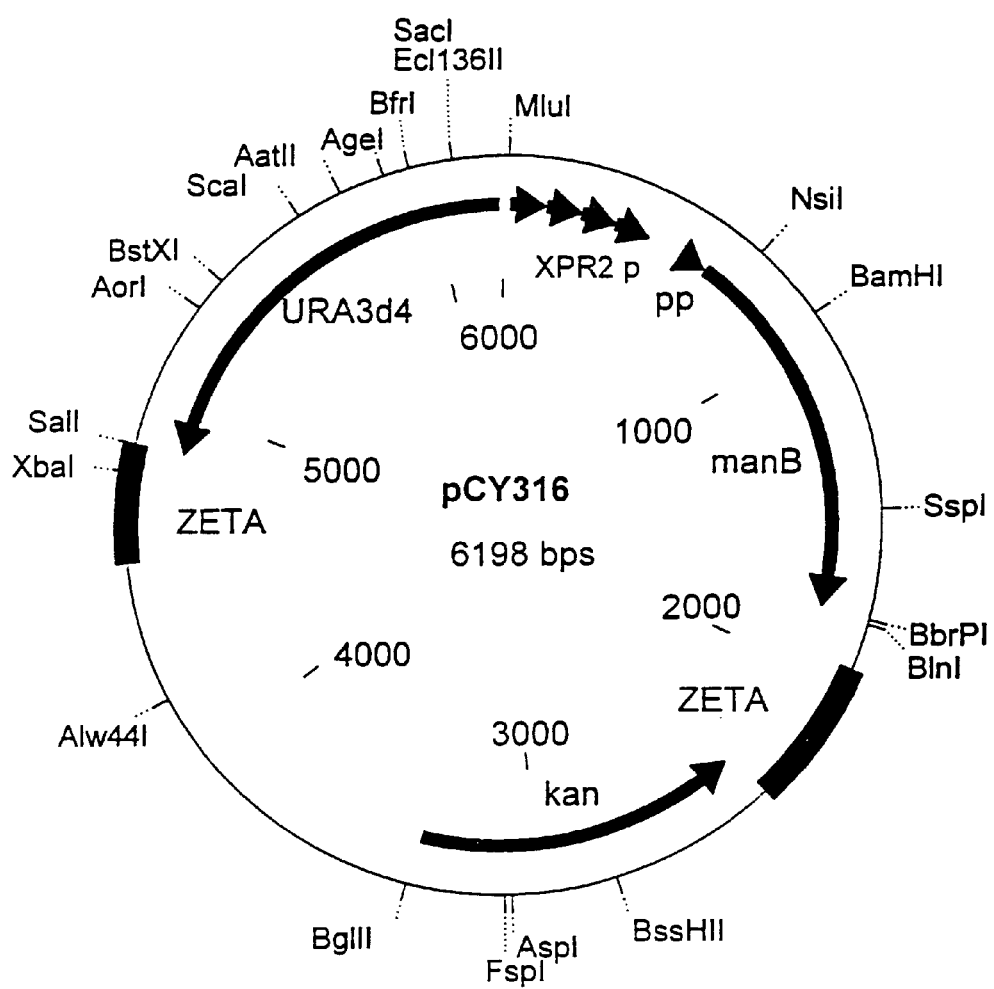
FIGURE 7: Physical map of plasmid pCY316

SEQUENCE LISTING

<160> NUMBER OF SEQ ID NOS: 25

<210> SEQ ID NO 1
<211> LENGTH: 1486
<212> TYPE: DNA
<213> ORGANISM: Coffea arabica

<400> SEQUENCE: 1

```
gtgaccagac tctagttcga agcaacaaat taatagctat atcaatcact caatataatc      60
aatgatgtcc agagaaaaga gtctcttgtt aaggtgctgt tctctttcct tggctctttt     120
cattcttctc ggtgttggag agggacatgg tgaaattgcg agtaatagta ccagcagcag     180
cagcttcagc tttgtcaaaa ctaggggaac tgagtttgtg atgaatggga ggccattata     240
cctcaacggc ttcaatgcat attggttaat gtacatggca tctgatccat ctacgaggac     300
gaaggtatca accaccttcc aacaagcttc aagtatgga atgaatgcag ccagaacttg      360
ggctttcagc gacggtggct atagggcttt gcaacaatct cctggttcct acaacgagga     420
catgttcaaa ggtttggatt cgtagtttc agaagcaaag aagtacggga tccatctcat      480
actcactttg gtcaacaact gggaaggtta cgggggaaag aaacaatatg tccagtgggc     540
gagagatcaa ggacactact tgaacaatga tgatgacttt tttaccgatc caattgtcag     600
aggctacttc aaaaaccaca tcaagactgt tctcacaaga atcaactcca taacgggact     660
tgcatacaaa gacgatccga ccatatttgc atgggagcta atgaatgaac ctcgttgcca     720
aagtgaccta tctggaaaag ctattcagga ttggatctca gaaatggcaa ctcatgtcaa     780
gtccatcgat agcgatcacc tcctagacat tggtcttgaa ggattttatg gagagtctgt     840
gccccaaaag aaggaatata atcctggtta ccaagttggg actgacttta tttccaataa     900
tcgcatagta caagtggatt ttgccaccat tcatttgtat cctgaccaat gggtacccaa     960
ttcgaatgat gagactcaag cacaatttgt ggatagatgg atcaaagagc acatagatga    1020
ttccaaatat ttgctcgaga agccacttct gttgaccgaa ttcggcaagt cttcaagatc    1080
acctgggtac caagtcgcca aaagggatgc gtatttatca catatatacg ataccatcta    1140
cgcttgtgca gcaactcgtg gcggcggcgt atgtggtggt aacctctttt ggcaagtcat    1200
ggctccaggg atggaaagtt ggggcgatgg atatgagatt gtcttggaag agaacccttc    1260
cactgtagga gtaattgctc aacaatccaa caggctatca tctcttacct aaatatggtt    1320
ggcaccaaat ctcaatgatg ttaagagcct actaagaatt catactacaa attctgaaaa    1380
taaaacagtt tttctaggtc ttatgtgaca ttattgtatc aattattaat ttgatactta    1440
aagtatcaat tcataacgag ttattacccg tgtatttgca cattca                   1486
```

<210> SEQ ID NO 2
<211> LENGTH: 416
<212> TYPE: PRT
<213> ORGANISM: Coffea arabica

<400> SEQUENCE: 2

```
Met Met Ser Arg Glu Lys Ser Leu Leu Leu Arg Cys Cys Ser Leu Ser
 1               5                  10                  15

Leu Ala Leu Phe Ile Leu Leu Gly Val Gly Glu Gly His Gly Glu Ile
             20                  25                  30

Ala Ser Asn Ser Thr Ser Ser Ser Phe Ser Phe Val Lys Thr Arg
         35                  40                  45

Gly Thr Glu Phe Val Met Asn Gly Arg Pro Leu Tyr Leu Asn Gly Phe
     50                  55                  60

Asn Ala Tyr Trp Leu Met Tyr Met Ala Ser Asp Pro Ser Thr Arg Thr
 65                  70                  75                  80

Lys Val Ser Thr Thr Phe Gln Gln Ala Ser Lys Tyr Gly Met Asn Ala
                 85                  90                  95
```

-continued

```
Ala Arg Thr Trp Ala Phe Ser Asp Gly Gly Tyr Arg Ala Leu Gln Gln
            100                 105                 110

Ser Pro Gly Ser Tyr Asn Glu Asp Met Phe Lys Gly Leu Asp Phe Val
        115                 120                 125

Val Ser Glu Ala Lys Lys Tyr Gly Ile His Leu Ile Leu Thr Leu Val
130                 135                 140

Asn Asn Trp Glu Gly Tyr Gly Gly Lys Lys Gln Tyr Val Gln Trp Ala
145                 150                 155                 160

Arg Asp Gln Gly His Tyr Leu Asn Asn Asp Asp Phe Phe Thr Asp
                165                 170                 175

Pro Ile Val Arg Gly Tyr Phe Lys Asn His Ile Lys Thr Val Leu Thr
            180                 185                 190

Arg Ile Asn Ser Ile Thr Gly Leu Ala Tyr Lys Asp Asp Pro Thr Ile
            195                 200                 205

Phe Ala Trp Glu Leu Met Asn Glu Pro Arg Cys Gln Ser Asp Leu Ser
        210                 215                 220

Gly Lys Ala Ile Gln Asp Trp Ile Ser Glu Met Ala Thr His Val Lys
225                 230                 235                 240

Ser Ile Asp Ser Asp His Leu Leu Asp Ile Gly Leu Glu Gly Phe Tyr
                245                 250                 255

Gly Glu Ser Val Pro Gln Lys Lys Glu Tyr Asn Pro Gly Tyr Gln Val
            260                 265                 270

Gly Thr Asp Phe Ile Ser Asn Asn Arg Ile Val Gln Val Asp Phe Ala
            275                 280                 285

Thr Ile His Leu Tyr Pro Asp Gln Trp Val Pro Asn Ser Asn Asp Glu
        290                 295                 300

Thr Gln Ala Gln Phe Val Asp Arg Trp Ile Lys Glu His Ile Asp Asp
305                 310                 315                 320

Ser Lys Tyr Leu Leu Glu Lys Pro Leu Leu Leu Thr Glu Phe Gly Lys
                325                 330                 335

Ser Ser Arg Ser Pro Gly Tyr Gln Val Ala Lys Arg Asp Ala Tyr Leu
            340                 345                 350

Ser His Ile Tyr Asp Thr Ile Tyr Ala Cys Ala Ala Thr Arg Gly Gly
        355                 360                 365

Gly Val Cys Gly Gly Asn Leu Phe Trp Gln Val Met Ala Pro Gly Met
370                 375                 380

Glu Ser Trp Gly Asp Gly Tyr Glu Ile Val Leu Glu Glu Asn Pro Ser
385                 390                 395                 400

Thr Val Gly Val Ile Ala Gln Gln Ser Asn Arg Leu Ser Ser Leu Thr
                405                 410                 415

<210> SEQ ID NO 3
<211> LENGTH: 22
<212> TYPE: PRT
<213> ORGANISM: Coffea arabica

<400> SEQUENCE: 3

Ser Phe Ser Phe Val Lys Thr Arg Gly Thr Glu Phe Val Met Asn Gly
1               5                   10                  15

Arg Pro Leu Tyr Leu Asn
            20

<210> SEQ ID NO 4
<211> LENGTH: 10
<212> TYPE: PRT
<213> ORGANISM: Coffea arabica
```

-continued

```
<400> SEQUENCE: 4

Thr Trp Ala Phe Ser Asp Gly Gly Tyr Arg
1               5                  10

<210> SEQ ID NO 5
<211> LENGTH: 17
<212> TYPE: PRT
<213> ORGANISM: Coffea arabica

<400> SEQUENCE: 5

Glu Tyr Asn Pro Gly Tyr Gln Val Gly Thr Asp Phe Ile Ser Asn Asn
1               5                  10                  15

Arg

<210> SEQ ID NO 6
<211> LENGTH: 18
<212> TYPE: DNA
<213> ORGANISM: artificial sequence
<220> FEATURE:
<223> OTHER INFORMATION: synthetic nucleotide Man 202
<220> FEATURE:
<221> NAME/KEY: misc_feature
<222> LOCATION: (3)..(3)
<223> OTHER INFORMATION: any
<220> FEATURE:
<221> NAME/KEY: misc_feature
<222> LOCATION: (6)..(6)
<223> OTHER INFORMATION: any
<220> FEATURE:
<221> NAME/KEY: misc_feature
<222> LOCATION: (15)..(15)
<223> OTHER INFORMATION: any

<400> SEQUENCE: 6
ggnacngart tygtnatg                                                18

<210> SEQ ID NO 7
<211> LENGTH: 17
<212> TYPE: DNA
<213> ORGANISM: artificial sequence
<220> FEATURE:
<223> OTHER INFORMATION: synthetic nucleotide man 203
<220> FEATURE:
<221> NAME/KEY: misc_feature
<222> LOCATION: (12)..(12)
<223> OTHER INFORMATION: any

<400> SEQUENCE: 7
ccrtcrctra angccca                                                 17

<210> SEQ ID NO 8
<211> LENGTH: 19
<212> TYPE: DNA
<213> ORGANISM: artificial sequence
<220> FEATURE:
<223> OTHER INFORMATION: synthetic nucleotide man 214

<400> SEQUENCE: 8
atcaaccacc ttccaacaa                                               19

<210> SEQ ID NO 9
<211> LENGTH: 18
<212> TYPE: DNA
<213> ORGANISM: artificial sequence
<220> FEATURE:
<223> OTHER INFORMATION: synthetic oligonucleotide man 215
```

```
<400> SEQUENCE: 9
taccttcgtc ctcgtaga                                                    18

<210> SEQ ID NO 10
<211> LENGTH: 20
<212> TYPE: DNA
<213> ORGANISM: artificial sequence
<220> FEATURE:
<223> OTHER INFORMATION: synthetic nucleotide T3

<400> SEQUENCE: 10
aattaaccct cactaaaggg                                                  20

<210> SEQ ID NO 11
<211> LENGTH: 22
<212> TYPE: DNA
<213> ORGANISM: artificial sequence
<220> FEATURE:
<223> OTHER INFORMATION: synthetic oligonucleotide T7

<400> SEQUENCE: 11
gtaatacgac tcactatagg gc                                               22

<210> SEQ ID NO 12
<211> LENGTH: 21
<212> TYPE: DNA
<213> ORGANISM: artificial sequence
<220> FEATURE:
<223> OTHER INFORMATION: synthetic oligonucleotide man 300

<400> SEQUENCE: 12
gtgaccagac tctagttcga a                                                21

<210> SEQ ID NO 13
<211> LENGTH: 22
<212> TYPE: DNA
<213> ORGANISM: artificial sequence
<220> FEATURE:
<223> OTHER INFORMATION: synthetic oligonucleotide man 301

<400> SEQUENCE: 13
tgaatgtgca aatacacggg ta                                               22

<210> SEQ ID NO 14
<211> LENGTH: 40
<212> TYPE: DNA
<213> ORGANISM: artificial sequence
<220> FEATURE:
<223> OTHER INFORMATION: primer B262

<400> SEQUENCE: 14
atatatccat ggtgagcttc agctttgtca aaactagggg                            40

<210> SEQ ID NO 15
<211> LENGTH: 35
<212> TYPE: DNA
<213> ORGANISM: artificial sequence
<220> FEATURE:
<223> OTHER INFORMATION: primer B260

<400> SEQUENCE: 15
atatatgtcg acggtaagag atgatagcct gttgg                                 35

<210> SEQ ID NO 16
<211> LENGTH: 20
```

```
<212> TYPE: DNA
<213> ORGANISM: artificial sequence
<220> FEATURE:
<223> OTHER INFORMATION: primer "pET-For"

<400> SEQUENCE: 16
tagttattgc tcagcggtgg                                              20

<210> SEQ ID NO 17
<211> LENGTH: 20
<212> TYPE: DNA
<213> ORGANISM: artificial sequence
<220> FEATURE:
<223> OTHER INFORMATION: primer "pET-Rev"

<400> SEQUENCE: 17
agcggataac aattcccctc                                              20

<210> SEQ ID NO 18
<211> LENGTH: 36
<212> TYPE: DNA
<213> ORGANISM: artificial sequence
<220> FEATURE:
<223> OTHER INFORMATION: primer B452

<400> SEQUENCE: 18
tcaaaggaat tctatcaatg aatattcgtc cattgc                            36

<210> SEQ ID NO 19
<211> LENGTH: 30
<212> TYPE: DNA
<213> ORGANISM: artificial sequence
<220> FEATURE:
<223> OTHER INFORMATION: primer B543

<400> SEQUENCE: 19
gggtttgtcg acttctgcga ggtgcagggc                                   30

<210> SEQ ID NO 20
<211> LENGTH: 49
<212> TYPE: DNA
<213> ORGANISM: artificial sequence
<220> FEATURE:
<223> OTHER INFORMATION: primer B281

<400> SEQUENCE: 20
ccggcctctt cggccgccaa gcgaagcttc agctttgtca aaactaggg              49

<210> SEQ ID NO 21
<211> LENGTH: 47
<212> TYPE: DNA
<213> ORGANISM: artificial sequence
<220> FEATURE:
<223> OTHER INFORMATION: primer B282

<400> SEQUENCE: 21
ggcccacgtg gccttagtgg tggtgggtaa gagatgatag cctgttg                47

<210> SEQ ID NO 22
<211> LENGTH: 26
<212> TYPE: DNA
<213> ORGANISM: artificial sequence
<220> FEATURE:
<223> OTHER INFORMATION: primer B360

<400> SEQUENCE: 22
```

```
gaacctcgtt gccaaagtga cctatc                                              26

<210> SEQ ID NO 23
<211> LENGTH: 26
<212> TYPE: DNA
<213> ORGANISM: artificial sequence
<220> FEATURE:
<223> OTHER INFORMATION: primer B361

<400> SEQUENCE: 23
caatgtctag gaggtgatcg ctatcg                                              26

<210> SEQ ID NO 24
<211> LENGTH: 24
<212> TYPE: DNA
<213> ORGANISM: artificial sequence
<220> FEATURE:
<223> OTHER INFORMATION: primer B358

<400> SEQUENCE: 24
gccagccaca gattttcact ccac                                                24

<210> SEQ ID NO 25
<211> LENGTH: 26
<212> TYPE: DNA
<213> ORGANISM: artificial sequence
<220> FEATURE:
<223> OTHER INFORMATION: primer B359

<400> SEQUENCE: 25
gaggaacgca tatacagtaa tcatag                                              26
```

COFFEE MANNANASE

CROSS-REFERENCE TO RELATED APPLICATION

This application is a continuation of the U.S. National Stage designation of International application PCT/EP01/01549 filed Feb. 13, 2001, the content of which is expressly incorporated herein by reference thereto.

FIELD OF THE INVENTION

The present invention relates to the use of fragments of coffee DNA encoding at least one enzyme involved in the hydrolysis of polysaccharides consisting at least of simple or branched mannan molecules linked to each other via a β (1→4) linkage.

BACKGROUND ART

Polysaccharides which contain mannose are frequently present in the cell walls of higher plants, in particular in leguminous plants, and are considered to be a carbohydrate store in the seeds.

In several plants, it has been shown that endo-α-mannanase activity is mainly detected in the endosperm of seeds undergoing germination (Bewley, Trends Plant Sci 2, 464–469, 1997).

In the coffee bean, galactomannans in particular are found. The latter represent approximately 24% of the dry weight of the bean (Bradbury and Halliday, J Agric Food Chem 38, 389–392, 1990). These polysaccharides consist of a linear chain of mannosyl residues which are linked to each other via β-1→4 type linkages and to which are attached α-galactosyl residue monomers. It is also known that the enzyme named endo-β-mannanase (E.C 3.2.1.78) is a hydrolase which degrades (1→4)-β-mannan polymers, thus facilitating the exit of the rootlet during germination and releasing small oligosaccharides which are then used as a source of energy for the growth of the young plant.

In industrial processes, during the treatment of coffee, the mannan molecules and their derivatives constitute a considerable portion of the insoluble sediments. In addition, the fraction of these molecules which dissolves during the first extraction (approximately 50%) is also very poorly soluble, and is therefore responsible for the majority of the secondary precipitations which occur during the subsequent steps. In patent EP 0676145A, therefore, it has been demonstrated that it is possible to hydrolyse coffee galactomannans using an immobilized mannanase extracted from *Aspergillus niger*.

EP application No. 98203742.6, itself, proposes the use of fragments of coffee DNA encoding at least one endo-β-mannanase involved in the hydrolysis of polysaccharides consisting at least of simple or branched mannan molecules linked to each other via a β (1→4) linkage.

It has, however, appeared advantageous to isolate other enzymes and genes derived from the coffee bean.

SUMMARY OF THE INVENTION

To this effect, a subject of the present invention is any fragment of DNA derived from coffee encoding at least one enzyme involved in the hydrolysis of such polysaccharides, which has the nucleic acid sequence SEQ ID NO: 1 or which is homologous to or hybridizes to a fragment of DNA having the nucleic acid sequence SEQ ID NO: 1.

The present invention also relates to the use of all or part of such fragments of DNA as a primer for carrying out a PCR or as a probe for detecting, in vitro, or modifying, in vivo, at least one coffee gene encoding at least one endo-β-mannanase.

The present invention also relates to any protein derived from the coffee bean, which is encoded by such a coffee gene and involved in the hydrolysis of polysaccharides consisting at least of simple or branched mannan molecules linked to each other via a β (1→4) linkage, and which has the amino acid sequence SEQ ID NO: 2 or any amino acid sequence homologous to the latter.

Another subject of the invention relates to any microorganism and any plant cell comprising, integrated into its genome or by means of a plasmid which can replicate, a fragment of DNA according to the present invention.

Finally, the invention relates to a dietary, cosmetic or pharmaceutical composition comprising a fragment of DNA or a protein according to the invention.

DESCRIPTION OF THE FIGURES

FIG. 1 represents a protein alignment of the *Aspergillus aculeatus, Trichoderma reesei* and *Lycopersicon esculentum* (tomato) endo-β-mannanases with mannanase A (Marraccini and Rogers, EP No. 98203742.6) and the coffee mannanase according to the present invention (mannanase B—SEQ ID 2).

FIG. 3 represents a map of the plasmid pDP580.

FIG. 4 represents a map of the plasmid pDP588.

FIG. 5 represents the analysis by SDS-PAGE gel electrophoresis of the expression of the ManB protein in *E. coli*, after induction by adding IPTG.

FIG. 6 represents a map of the plasmid pNFF296.

FIG. 7 represents a map of the plasmid pCY316.

DETAILED DESCRIPTION OF THE INVENTION

Figure 2:
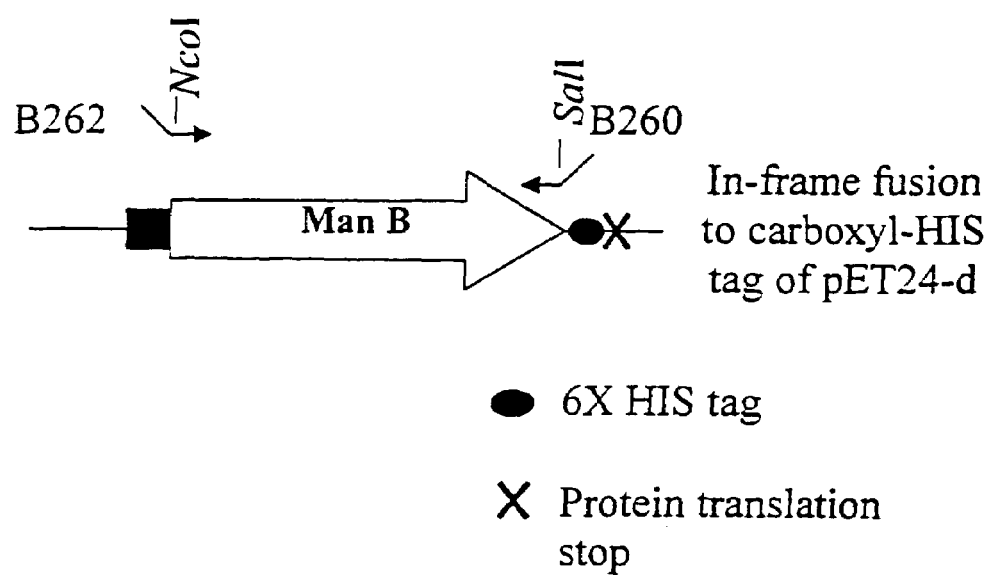
FIG. 2 represents a scheme which makes it possible to position the synthetic oligonucleotides used for amplifying the mature ManB protein including the HIS tag group at its carboxy-terminal (C-ter.) end.

For the purposes of the present invention, the term "homologous sequence" is intended to mean any nucleic acid or amino acid sequence having an identical function, which differs from the sequences according to the invention only by the substitution, deletion or addition of a small number of nucleic acid bases or of amino acids, for example 1 to 500 base pairs (bp) or 1 to 150 amino acids.

In this context, two DNA sequences which, because of the degeneracy of the genetic code, encode the same polypeptide will in particular be considered to be homologous. Similarly, two functional proteins which are recognized by the same antibody, the ratio of the values of intensity of recognition of the two proteins by the antibody not exceeding 100, for example, will be considered to be homologous.

Also considered to be a homologous sequence will be that sequence which has more than 70% homology with the sequences according to the invention, in particular more than 80% or 90%. In the latter case, the homology is determined by the ratio between the number of bases or of amino acids of a homologous sequence which are identical to those of a sequence according to the invention, and the total number of bases or of amino acids of said sequence according to the invention.

For the purposes of the present invention, the term "fragment which hybridizes" is intended to mean any fragment capable of hybridizing to the fragments according to the invention by the method of Southern Blot (Sambrook et al., Molecular Cloning, A Laboratory Manual, Cold Spring Harbor Laboratory Press, USA, 1989, chapters 9.31 to 9.58). Preferably, the hybridization is carried out under stringent conditions so as to avoid aspecific or relatively unstable hybridizations.

Finally, the term "fragment" or "fragment of DNA" should be understood to be a double-stranded DNA of chromosomal origin which can be synthesized, reproduced in vitro for example by the known method termed "Polymerase Chain Reaction", or reproduced in vivo in a bacterium of the *Escherichia coli* type, for example.

In the remainder of the description, the sequences SEQ ID NO: refer to the sequences given in the sequence listing hereinafter. The synthetic oligonucleotides SEQ ID NO: 6 to SEQ ID NO: 25 mentioned in the description and given in the sequence listing hereinafter are provided by Eurogentec (Parc Scientifique du Sart Tilman [Sart Tilman Scientific Park]-4102 Seraing-Belgium).

It has been possible to show that all or part of the sequence SEQ ID NO: 1 makes it possible, subsequent to a transformation, to hydrolyse polysaccharides consisting at least of pure or branched mannan molecules linked to each other via a β (1→4) linkage in a host cell, such as a plant cell or a microorganism.

The present invention relates to any fragment of DNA having the nucleic acid sequence SEQ ID NO: 1 or any fragment of DNA which is homologous to or hybridizes to this nucleic acid sequence encoding at least one enzyme involved in the hydrolysis of polysaccharides consisting at least of pure or branched mannan molecules linked to each other via a β (1→4) linkage.

The enzyme is preferably an endo-β-mannanase having the amino acid sequence SEQ ID NO: 2, or any amino acid sequence homologous to the latter. The endo-β-mannanase can contain at least one of the following amino acid sequences: SEQ ID NO: 3 to 5.

Preferably, the invention relates to the fragment of DNA delimited by nucleotides 62 to 1312 of the nucleic acid sequence SEQ ID NO: 1.

The present invention also relates to the novel enzymes encoded by the genes of the sequence SEQ ID NO: 1, in particular the sequences which are homologous to them. It is thus possible to envisage using them to modify or degrade such polysaccharides in vitro, for example. For this, it is preferable to purify at least one of these enzymes, by conventionally over-expressing their gene in a bacterium and isolating them conventionally, by precipitation and/or chromatography of the culture medium, for example.

The invention also relates to the use of all or part of fragments of DNA according to the invention, in particular as a primer for carrying out a PCR or as a probe for detecting, in vitro, or modifying, in vivo, at least one coffee gene encoding at least one endo-β-mannanase. At least 10 base pairs are preferably used.

Moreover, a subject of the present invention is also a protein derived from the coffee bean, which is encoded by a coffee gene and involved in the hydrolysis of polysaccharides consisting at least of pure or branched mannan molecules linked to each other via a β (1→4) linkage, and which has the amino sequence SEQ ID NO: 2 or any amino acid sequence homologous to the latter. The endo-β-mannanase can contain at least one of the following amino acid sequences: SEQ ID NO: 3 to 5.

Another subject of the present invention relates to process for hydrolysing polysaccharides consisting at least of pure or branched mannan molecules linked to each other via a β (1→4) linkage, in which (1) a fragment of DNA encoding the enzymes according to the invention is cloned into a vector, said vector also comprising a sequence allowing autonomous replication or integration in a host cell, (2) a host cell is transformed with said vector, and then (3) the transformed host cell is cultured under conditions suitable for the hydrolysis of such polysaccharides.

The present invention therefore opens up the possibility of using fragments of DNA according to the invention to modify the production of polysaccharides consisting at least of pure or branched mannan molecules linked to each other via a β (1→4) linkage in a host cell, in particular a coffee bean cell. It is thus possible to envisage expressing or over-expressing DNAs according to the invention, in a coffee bean cell, in order to produce such polypeptides intended to modify the aroma and the structure of the coffee beans, for example.

Finally, the present invention also provides novel enzymes involved in the hydrolysis of such polysaccharides. These enzymes can thus be advantageously used to synthesize or modify such polysaccharides, in vitro.

The present invention also relates to a plant cell comprising, integrated into its genome or by means of a recombinant vector, a fragment of DNA having the nucleotide sequence SEQ ID NO: 1, or a fragment of DNA having a nucleic acid sequence which is homologous to or hybridizes to the nucleic acid sequence SEQ ID NO: 1, or a fragment of DNA comprising at least nucleotides 62 to 1312 of the nucleic acid sequence SEQ ID NO: 1.

The plant cell is preferably a coffee cell. It is possible in particular to choose, as coffee cells, cells derived from a plant of *Coffea canephora* var. *robusta*, *Coffea arabica* or any other species of the *Coffea* genus.

The present invention also relates to any plant or any seed consisting of plant cells comprising, integrated into its genome or by means of a recombinant vector, a fragment of DNA having the nucleotide sequence SEQ ID NO: 1, or a fragment of DNA having a nucleic acid sequence which is homologous to or hybridizes to the nucleic acid sequence SEQ ID NO: 1, or a fragment of DNA comprising at least nucleotides 62 to 1312 of the nucleic acid sequence SEQ ID NO: 1.

Any microorganism comprising, integrated into its genome or by means of a plasmid which can replicate, a fragment of DNA according to the invention such that it expresses at least one enzyme involved in the hydrolysis of polysaccharides consisting at least of pure or branched mannan molecules linked to each other via a β (1→4) linkage is also a subject of the present invention.

Another subject of the invention relates to any dietary, cosmetic or pharmaceutical composition comprising a fragment of DNA according to the invention or a protein according to the invention.

Finally, the present invention relates to a process for treating coffee beans, in which all or part of the protein according to the invention is used. It is in particular possible to use all or part of the protein according to the invention to increase the percentage of solids extracted, during the treatment of coffee beans. Using all or part of the protein according to the invention, it is thus possible to increase the extraction yield while at the same time decreasing the amount of sediment.

After over-expression of the fragment of DNA according to the invention in a microorganism, in a fungus or in an undifferentiated plant cell, the sediments can be treated with the more or less purified enzyme, so as to thus increase the extraction yields.

After over-expression of the fragment of DNA according to the invention in a microorganism, in a fungus or in an undifferentiated plant cell, it is also possible to treat the coffee liquor, so as to decrease the sedimentation due to the mannans which gel.

The present invention is described in more detail hereinafter with the aid of the further description which will follow and which refers to examples of production of fragments of DNA, of recombinant plasmids and of transformed bacteria according to the invention. It goes without saying, however, that these examples are given by way of illustration of the subject of the invention for which they in no way constitute a limitation. The handling of the DNA, the cloning and the transformation of bacterial cells are, in the absence of instructions to the contrary, carried out according to the protocols described in the manual by Sambrook et al., mentioned above. The percentages are given by weight, unless otherwise indicated.

EXAMPLE 1

Measurement of the Peak of Activity of endo-β-mannanase During Germination

Beans of the *Coffea arabica* var. *caturra* 2308 variety are harvested at the mature stage, depulped and dried for three days at room temperature. Next, the parchment skin of the beans is removed, and they are dried and then sterilized in order to be germinated in culture in vitro. To do this, they are placed in Rovral (0.12% v/v) for 1 hour, rinsed with sterile water, placed in a solution of calcium hypochlorite (6% w/v) to which a few drops of Teepol emulsifier are added, for 1 hour, and then rinsed 4 times with sterile water before being cultured in test-tubes on an agar-water medium. The germination occurs at 25° C. in the presence of light. The moment when the beans are placed on the agar bed is considered to be day after soaking zero (DAS=0).

The batches of beans are then harvested at various stages of germination (DAS 7, 14, 21, 28), and then are ground in liquid nitrogen. Next, the powder is homogenized in a proportion of 1 g per 5 ml, in an extraction buffer (200/100 mM phosphate-citrate, pH 5.0, 10 mM meta-bisulphite, $Na_2S_2O_5$, 5 mM EDTA and one tablet/50 ml of "Complete" protease inhibitor [Cat. No. 1 836 145, Roche Diagnostics GmbH, Sandhofer Strasse 116, Mannheim, GE] 1 tablet/50 ml), for 20 min at 4° C. The homogenate is then centrifuged at 12 000 g for 20 min at 4° C., and the supernatant is recovered and centrifuged a second time. The supernatant, corresponding to the crude enzymatic extract, is then aliquoted and frozen at −80° C.

The enzymatic activity of the endo-β-mannanase is assayed according to the following method. A 400 μl crude enzymatic extract is added to 1.6 ml of reaction buffer (100 mM NaCl, 200 mM sodium acetate, pH 5.0) containing AZCL-Galactomannan insoluble substrate (Cat. No. I-AZGMA, Megazyme International Ireland Ltd, Bray Business Park, Bray Co., Wicklow, Ireland) in a final quantity of 1% w/v. The reaction commences by adding the extract, and takes place at 37° C. with stirring. In order to calculate the initial slope of the reaction, a 400 μl aliquot of medium is removed every 15 min for 1 h, heated at 1000 for 5 min and then centrifuged at 12 000 g for 2 min. The optical density of the supernatant is measured at 590 nm and the specific activity is expressed in AU (optical absorption units).$min^{-1}$.mg protein$^{-1}$, after having assayed the protein concentration in each extract by the Bradford method (Bradford, Anal. Biochem. 72, 248–254, 1976). Thus, it is found that the activity is virtually zero during the first 14 days after soaking (DAS), and subsequently increases gradually up to a maximum peak around 28 DAS. After 28 DAS, the activity slowly decreases.

EXAMPLE 2

Endo-β-Mannanase Purification Steps

According to the results described above, the purification strategy is continued using 16 ml of a 28-DAS crude enzyme extract having an activity of around 0.2 AU.min$^{-1}$.mg protein$^{-1}\times 10^{-2}$, a total protein content of approximately 48 mg and a total activity of 9.6 AU.min$^{-1}\times 10^{-2}$.

1. Ammonium Sulphate Precipitation:

Initially, the crude enzymatic extract is fractionated by ammonium sulphate precipitation at 4° C. The ammonium sulphate is added slowly with stirring until a saturation level of 35% is obtained, and the solution is then centrifuged at 12 000 g at 4° C. for 20 min. The pellet thus obtained is taken up in a minimum (1 ml) of extraction buffer (see above). In this extract, the protein concentration is approximately 10 mg.ml$^{-1}$. The endo-β-mannanase specific activity is 0.9 AU.min$^{-1}$.mg$^{-1}\times 10^{-2}$, which corresponds to a 4-fold enrichment of the enzyme with respect to the crude extract and a recovery of 10 AU.min$^{-1}$ of the total activity, i.e. 100%.

2. Separation on a Hydrophobic Interaction Column

The sample described above is then separated on a hydrophobic interaction column (Hiload HR 16/10 phenyl sepharose High performance, Amersham Pharmacia Biotech UK Ltd, Amersham Place, Little Chalfont, Buckinghamshire, HP7 9NA, England). The column is pre-equilibrated with an equilibration buffer (50 mM sodium phosphate, 400 mM ammonium sulphate, pH 7.0). The sample (1 ml) is then injected onto the column, which is then washed with 5 column volumes of the equilibration buffer. A 0 to 99.5% gradient of water in 0.5 column volumes is applied, followed by another of 99.5 to 100% in 5 column volumes. The activity is mainly concentrated in three fractions, which are used to continue the purification. The purification yield of this step is around 80% with respect to the previous step. The specific activity is 27 AU.min$^{-1}$.mg$^{-1}$, i.e. an approximately 137-fold enrichment with respect to the crude extract. The total activity recovered is approximately 9 AU.min$^{-1}\times 10^{-2}$, i.e. 90% of the initial activity.

3. Separation by Ion Exchange Chromatography

The three fractions described above are mixed and concentrated and the buffer changed using Ultrafree tubes (Millipore, Bedford, Mass., USA, centrifugation at 4 000 g maximum). The volume recovered is 1 ml. This sample is injected onto a Resource Q (Amersham Pharmacia Biotech, England) anion exchange column pre-equilibrated with a 20 mM Tris/HCl, pH 8.0, buffer. The elution is carried out with a linear gradient of 0 to 1 M NaCl in 20 column volumes. The total activity recovered is present exclusively in two fractions. The purification yield of this step is 58% with respect to the previous step. The specific activity is 167 AU.min$^{-1}$.mg$^{-1}$, i.e. an approximately 836-fold enrichment with respect to the crude extract. The total activity recovered is 0.9 AU.min$^{-1}$, i.e. approximately 9% of the initial activity.

4. Separation by Gel Filtration Column

The two fractions recovered from the anion exchange column are concentrated to 100 µl by centrifugation at 4 000 g using the Ultrafree tubes (Millipore Co, 80 Ashby Road, Bedford, Mass., USA). This sample is injected onto a Superdex 75 HR 10/30 column (Amersham Pharmacia Biotech, England) pre-equilibrated with a 50 mM sodium phosphate, 150 mM NaCl, pH 7.0, buffer. The proteins are eluted with the same buffer, with a flow rate of 0.3 ml.min$^{-1}$. A calibration curve for the column is prepared under the same conditions using molecular weight standards. The endo-β-mannanase activity is distributed in two fractions, corresponding to a molecular weight of between 40 and 55 kDa. The purification yield of this final step is 48%. The specific activity is approximately 1 400 AU.min$^{-1}$.mg$^{-1}$, i.e. a 7 000-fold enrichment with respect to the crude extract. The total activity is 0.45 AU.min$^{-1}$, i.e. 4.5% of the initial activity.

5. Analyses by Bi-Dimensional Electrophoresis and Microsequencing of the Amino Acids of the Purified Enzyme The fractions described above with the enzymatic activity at column exit are analysed during the purification by bi-dimensional electrophoreses. To do this, the fractions are mixed and concentrated to 20 µl by centrifugation in the Ultrafree tubes (Millipore, USA) as described above. 105 µl of rehydration buffer (8 M urea, 3% w/v CHAPS, 0.8% v/v ampholines, 1% w/v DTT) are added to this volume, and a non-linear (pH 3.0 to 10.0) 7 cm gel strip (Immobiline Dry Strip, Amersham Pharmacia Biotech, England) is rehydrated according to the manufacturer's instructions. The proteins are then separated as a function of their isoelectric point (pI) using, for example, the IPGphore system (Amersham Pharmacia Biotech, England, employing a total number of 14 000 volt-hours.

Following the separation of the proteins as a function of their pI, they are then separated in a second dimension according to their molecular weights. This separation is carried out according to the recommendations of Hochstrasser et al. (Anal. Biochem, 173, 412–423, 1989) and of Gorg et al. (Electrophoresis, 8, 122–124, 1987). Thus, the gel strip of the first dimension is equilibrated in a first solution (6 M urea, 30% v/v glycerol, 2% w/v SDS, 2% DTT, 50 mM Tris-HCl, pH 8.0) for 5 min, and then equilibrated in a second solution (6 M urea, 30% v/v glycerol, 2% w/v SDS, 2.5% w/v iodoacetamide, 50 mM Tris-HCl, pH 8.0) for 10 min. The gel strip is then loaded into a 10–20% acrylamide concentration gradient gel (dimensions 10×10×0.75 cm) with a single well, and covered with an agarose solution (1% w/v agarose, 0.5% w/v SDS, traces of bromophenol blue) pre-heated at 90° C. and maintained at 40° C. The gel is mounted in a vertical electrophoresis system and is subjected to a voltage of 170 V for 2 h. After migration, the proteins are stained with silver according to the method of Bjellqvist et al. (Electrophoresis, 14, 1357–1365, 1993). The profile of the mixture of the final three fractions thus obtained shows the presence of a single group of proteins which consist of a line of 5 proteins with the same approximate molecular weight of 42 kDa, but with slight differences in pI, between pI 5.5 and 6. This estimation of pI is confirmed by the fact that the endo-β-mannanase activity is eluted from a chromatofocusing column (mono P HR 5/5—Amersham Pharmacia Biotech, England) at a pH of 5.7 (results not shown) and also by the estimation of the theoretical pI (5.8) of the mature protein (see below).

The proteins thus purified are analysed by microsequencing the amino acids. To do this, they are transferred onto a PVDF membrane ("Problot", Perkin Elmer Applied Biosystems Division, 850 Lincoln Center Drive, Foster City, Calif. 94404, USA) using, for example, a Trans-Blot transfer cell (Bio-Rad, 2000 Alfred Drive, Hercules, Calif. 94547, USA). Thus, following the separation of the second dimension, the gel is recovered and shaken in a transfer solution (10% v/v methanol, 10 MM NaOH-CAPS, pH 11.0) for 10 min. During this time, two foam supports, two pieces of Whatman paper and a PCDF-Problot membrane (Perkin Elmer Applied Biosystem, USA) are wetted in the same solution. The gel, the membrane and the supports are mounted in the Trans-Blot system according to the manufacturer's (Bio-Rad, USA) instructions, and the transfer is carried out under a current of 100 V for one hour at a temperature of 4° C. At the end of the transfer, the proteins transferred onto the membrane are revealed with light Coomassie blue staining according to the instructions of the Problot membrane manufacturer. The various proteins are excised from the membrane, mixed and sequenced together. The N-terminal sequencing of the purified proteins and of the internal peptides is carried out with a Beckmann automatic sequencer (Beckmann Instruments Inc., 250 Harbor Boulevard Box 3100, Fullerton, Calif., 92634 USA) according to the methods described in Teixeira et al. (Electrophoresis, 18, 156–162, 1997).

Three sequences are obtained by this method; a 22-amino acid N-terminal sequence, called SEQ ID NO: 3, and two others concerning independent internal peptides, obtained by trypsin digestion, of 10 and 17 amino acids, respectively, described in the sequences SEQ ID NO: 4 and 5.

None of the sequences obtained have ambiguities and show that the three proteins, which make up the line described above, are isozymes of the endo-β-mannanase which share a sequence which is identical in the regions analysed. The sequences SEQ ID NO: 3, 4 and 5 correspond respectively to the residues 41 to 62, 99 to 108 and 265 to 281 of sequence SEQ ID NO: 2.

EXAMPLE 3

βIsolation of the Full-Length cDNA Encoding the Coffee endo-β-mannanase Purified from Beans Undergoing Germination 1. Isolation of the Total RWAs and of the poly A+ Messenger RNAs from the Germinating Coffee Bean The coffee beans (*Coffea arabica* var. *caturra* 2308) are harvested at the mature stage and germinated in vitro as described above.

The total RNAs of beans are extracted after 22 days of germination (DAS 22). To do this, the bean is rapidly ground in liquid nitrogen and the powder obtained is resuspended in 8 ml of buffer at pH 8.0 containing 100 mM Tris HCl, 0.1% w/v of SDS and 0.5% v/v of β-mercaptoethanol, it is homogenized with one volume of phenol saturated with 100 mM Tris HCl, pH 8.0, and then it is centrifuged at 12 000 g for 10 min at 4° C., so as to extract the aqueous phase, which is centrifuged (i) once with an equivalent volume of phenol, (ii) twice with an equivalent volume of phenol:chloroform (1:1) and (iii) twice with an equivalent volume of chloroform (Rogers et al., Plant Physiol. Biochem. 37, 261–272, 1999).

The total nucleic acids are then precipitated for 1 h at −20° C. by adding to the aqueous phase ¹⁄₁₀ of a volume of 3 M sodium acetate, pH 5.2, and 2.5 volumes of ethanol.

The resulting mixture is then centrifuged at 12 000 g for 30 min at 4° C., and the pellet is taken up in 10 ml of $H_2O$, before re-precipitating the nucleic acids in the presence of LiCl (2 M final) and of ethanol (2.5 volumes).

After centrifugation, the pellet of total RNAs is taken up in 1 ml of $H_2O$ and it is digested for 1 h at 37° C. with RQ1 DNAse (Promega Corporation, 2800 Woods Hollow Road, Madison, Wis. 53711 USA) in order to eliminate any trace of DNA, and then the total RNAs are deproteinated by treating with phenol and with chloroform, before precipitating them in the presence of sodium acetate as described above.

The total RNAs are then taken up in 500 µl of $H_2O$, and they are quantified by spectrophotometric assay at 260 nm. Their quality is analysed by agarose gel electrophoresis in the presence of formaldehyde.

To do this, the poly A+ messenger RNAs (mRNAs) are then purified from 500 µg of total RNAs using the oligotex-dT purification system (Qiagen INC., 9600 De Soto Avenue, Chatsworth, Calif., 91311 USA), and then the quantity of messenger RNAs is evaluated using the DNA Dipstick kit (InVitrogen BC, De Schelp 12, 9351 NV Leek, the Netherlands).

2. Construction and Screening of the cDNA Library

The synthesis of complementary DNA (cDNA), required for constructing the libraries, is carried out according to the recommendations supplied in the "Riboclone cDNA synthesis system M-MLV (H–)" kit (Promega, USA), except for the EcoRI linker ligation step. This makes it possible to clone these cDNAs directly into the unique SrfI site of the vector pPCR-Script Amp SK(+) (Stratagene, 11011 North Torrey Pines Road, La Jolla, Calif. 92037, USA). The efficiency of this cDNA synthesis reaction is monitored by adding alpha-($^{32}$P)-dCTP during the synthesis of the two DNA strands.

After migration on alkaline agarose gel (Sambrook et al., Molecular Cloning, A Laboratory Manual, Cold Spring Harbor Laboratory Press, USA, 1989), the length of the neosynthesized cDNAs is estimated as ranging from 0.2 to more than 4.3 kb. The quantifications, using the DNA Dipstick kit (InVitrogen, the Netherlands), show that approximately 100 ng of cDNA are synthesized from 1 µg of mRNA.

The cDNAs ligated into the vector pPCR-Script Amp SK(+) (Stratagene, USA) were used to transform the *Escherichia coli* (*E. coli*) strain XL2-Blue MRF' (Stratagene, USA). The bacteria which contain recombinant vectors are selected on plates of LB (Luria-Bertani) medium containing 100 µg.ml$^{-1}$ of ampicillin, and in the presence of IPTG and of X-Gal (Sambrook et al., 1989). The plasmids of this cDNA library are then extracted from an overnight culture, corresponding to a mixture of transformants, in the presence of 25 ml of LB medium containing 100 µg.ml$^{-1}$ of ampicillin, and using the "QiaFilter Plasmid MidiKit" (Qiagen INC., USA).

3. Isolation of the cDNA Encoding the Coffee Endo-β-Mannanase

This germinating bean cDNA library was tested by PCR using synthetic oligonucleotides deduced from the result of the N-terminal and internal sequencing of the purified mannanase.

The degenerate synthetic oligonucleotides MAN 202, having the nucleic acid sequence SEQ ID NO: 6, and MAN 203, having the nucleic acid sequence SEQ ID NO: 7, are used. The synthetic oligonucleotide MAN 202 corresponds to amino acids 9 to 14 (GTEFVM) of the N-terminal sequence (SEQ ID NO: 3) of the purified mannanase. The synthetic oligonucleotide MAN 203 corresponds to the complementary sequence encoding amino acids WAFSDG located at position 2 to 7 of the internal peptide of the purified mannanase, corresponding to the sequence SEQ ID NO: 4.

The PCR reaction is carried out in the presence of 10 ng of plasmid from the cDNA library, in a final volume of 50 µl containing 50 mM KCl, 10 mM Tris-HCl, pH 8.8, 1.5 MM $MgCl_2$, 0.1 mg.ml$^{-1}$ gelatin, 0.2 mM of each dNTP, 0.25 mM of each oligonucleotide (MAN 202 and 203) and 3 units of Taq DNA polymerase (Stratagene, USA). The Robocycler 96 (Stratagene, USA) PCR machine equipped with a heating cover is used, and the reactions are incubated for 35 cycles (94° C.—1 min, 45° C.—1 min 30 s, 72° C.—2 min) followed by a final extension at 72° C. for 7 min. At the end of this reaction, a unique PCR product approximately 170 bp long is obtained, which was directly ligated into the vector pGEMT-easy, according to the supplier's (Promega, USA) recommendations. The ligation is then used to transform the *E. coli* strain XL2-Blue MRF' (Stratagene, USA). The bacteria which contain recombinant vectors are selected on plates of LB medium containing 100 µg.ml$^{-1}$ of ampicillin, and in the presence of IPTG and of X-Gal (Sambrook et al., 1989).

At the end of the transformation, a clone was isolated which contains the 170 bp fragment of cDNA cloned into the SfrI site of the vector pPCR-Script Amp SK(+) (Stratagene, USA). This PCR product was then sequenced according to the "T7 sequencing kit" protocol (Amersham Pharmacia Biotech, England), in the presence of alpha ($^{35}$S)-dATP. The analysis of its sequence shows that it is located between nucleotides 206 and 375 of the sequence SEQ ID NO: 1 and is bordered, at its 5' and 3' ends, by the sequences corresponding to the oligonucleotides MAN 202 and 203. From this analysis, it is deduced that this PCR product corresponds to a fragment of the cDNA effectively encoding the coffee endo-β-mannanase which was purified and sequenced as defined above. It is also noted that this cDNA is different from that which was cloned in the laboratory (EP No. 98203742.6), which suggests the existence of a multigene family encoding the coffee endo-β-mannanase.

In order to isolate the full-length cDNA of the coffee endo-β-mannanase, a series of PCR reactions are carried out, this time using synthetic oligonucleotides which are specific and deduced from the sequence of the 170 bp PCR product previously cloned. For this, the oligonucleotides MAN 214, having the nucleic acid sequence SEQ ID NO: 8, and MAN 215, having the nucleic acid sequence SEQ ID NO: 9, are used. The synthetic oligonucleotides MAN 214 and 215 correspond, respectively, to nucleotides 307 to 325 and 307 to 290 of the sequence SEQ ID NO: 1 and are positioned head-to-tail on this same sequence.

These PCR reactions use 10 ng of the cDNA library screened previously, the oligonucleotides MAN 214 and 215, and the universal oligonucleotides T3 and T7 specific for the cloning vector pPCR-Script Amp SK(+) (Stratagene, USA), which correspond to the sequences SEQ ID NO: 10 and 11, respectively. These primers are each located at approximately 100 bp from the SfrI cloning site of the vector pPCR-Script Amp SK(+), on either side. The PCR reactions are incubated according to the conditions described above, and with the following parameters: 40 amplification cycles (94° C.—1 min, 50° C.—1 min 30 s, 72° C.—3 min) followed by a final extension at 72° C. for 7 min.

After migration of the PCR products on agarose gel, the presence of a fragment of DNA of approximately 400 bp amplified during the MAN 215-T3 reaction and of a fragment of DNA of approximately 1.2 Kb amplified during the MAN 214-T7 reaction is observed. These fragments were cloned independently into the vector pGEMT-easy (Promega, USA), and then sequenced on both strands (Eurogentec Bel s.a.—Parc Scientifique du Sart Tilman [Sart Tilman Scientific Park]—4102 Seraing-Belgium). The analysis of the nucleic acid sequences shows that the PCR product amplified by the oligonucleotides MAN 215-T3 comprises the first 307 nucleotides of the sequence SEQ ID NO: 1, whereas the PCR product amplified by the oligonucleotides MAN 214-T7 comprises the last 1180 bases of the sequence SEQ ID NO: 1, and also a 26-residue poly A+ tail which is not shown on the sequence SEQ ID NO: 1.

In order to isolate the full-length cDNA of the coffee mannanase corresponding to the sequence SEQ ID NO: 1, a final PCR reaction was carried out using 20 ng of the plasmid DNA library and the synthetic oligonucleotides MAN 300 and 301. These primers correspond, respectively, to the sequences SEQ ID NO: 12 and 13 and are located at the 5' and 3' ends, respectively, of the sequence SEQ ID NO: 1. The primer MAN 301 was chosen to be located just upstream of the polyA+ tail present in the PCR fragment amplified with the oligonucleotides MAN 214-T7. This PCR reaction was carried out in a final volume of 50 µl containing 10 ng of cDNA library plasmid (DAS=22), 10 mM KCl, 6 mM $(NH_4)_2SO_4$, 20 mM Tris-HCl, pH 8, 0.1% Triton X-100, 2 mM $MgCl_2$, 0.2 mM of each dNTP, 10 µg/ml BSA, 0.25 µM of each oligonucleotide and 3 units of Pfu DNA polymerase (Stratagene, USA). The reaction is incubated for 45 cycles (94° C.—1 min, 45° C.—1 min 30 s, 72° C.—3 min) and followed by a final extension at 72° C. for 7 min.

At the end of this reaction, a single fragment of approximately 1 500 bp is amplified, which was cloned into the vector pPCR Script Amp SK(+), and then sequenced on both strands. Its sequence corresponds to the sequence SEQ ID NO: 1. By comparison in the databanks, it is deduced that this cDNA is full length and effectively encodes an endo-β-mannanase which comprises the protein sequences SEQ ID NO: 3 to 5 obtained previously from the purification of the endo-β-mannanase. It is also noted that this cDNA is different from the cDNA cloned previously in the laboratory (EP No. 98203742.6). It therefore constitutes a novel cDNA encoding the coffee endo-β-mannanase which was purified as described above. It is also noted that this sequence SEQ ID NO: 1 contains, without any nucleotide difference, all the sequences of the cloning intermediates isolated previously during the PCR amplifications of the germinating cDNA library.

4. Analysis of the Full-Length cDNA Encoding the Coffee Endo-β-Mannanase

The analysis of the nucleic acid sequence shows that this full-length cDNA contains a 61 bp transcribed, untranslated sequence at its 5' end, and a 174 bp 3' transcribed, untranslated sequence. It has no poly A+ tail at its 3' end since the synthetic oligonucleotide MAN 301 used above was precisely chosen upstream of this sequence. Within this 3' transcribed, untranslated sequence, the presence of AT-rich motifs which are presumed to be involved in polyadenylation mechanisms is observed. The presence of several inverted and direct repeat sequences, which might be involved in mechanisms of messenger RNA stability or of translation efficiency, for example (Gallie, Plant Mol Biol, 32, 145–158, 1996) is also noted.

The sequence SEQ ID NO: 1 contains an open reading frame of 417 codons (1251 bases), which begins with the ATG codon at position 62 and ends with a TAA codon (A at position 1312). The presence of a second translation-initiation codon at position 65 of the sequence SEQ ID NO: 1 is also noted. The protein deduced from this complementary DNA has a theoretical molecular weight of 46794 Da and a theoretical pI of 7.8. It also has a very hydrophobic protein segment which corresponds approximately to the first 30 amino acids of the sequence SEQ ID NO: 2. This protein sequence might correspond to a signal peptide containing the 40 amino acids of the sequence SEQ ID NO: 1 upstream of the sequence SEQ ID NO: 3 which corresponds to the N-terminal sequencing of the purified enzyme. In this case, the molecular weight of the protein is expected to be 42616 Da in its mature form, i.e. corresponding to the last 376 amino acids of the sequence SEQ ID NO: 2. In this case, its pI is estimated to be close to 5.8. These data are in agreement with those observed during the purification of the protein (see Example: 2, ♣5).

The existence of several potential glycosylation sites (Asn/X/Ser or Thr) is also noted. The first is located in the potential signal peptide, at position 35 to 37 of the sequence SEQ ID NO: 2, and is therefore presumed to be absent in the mature form of the mannanase. The second is located at the C-terminal position, at position 398 and 400 of the sequence SEQ ID NO: 2.

It is noted that the sequences SEQ ID NO: 3 to 5, which correspond to the protein sequencing carried out using the purified protein, are found, without any ambiguity, within the protein (SEQ ID NO: 2) deduced from the sequence SEQ ID NO: 1. For example, the sequence SEQ ID NO: 3 corresponds to amino acids 41 to 62 of SEQ ID NO: 2. Similarly, the sequences SEQ ID NO: 4 and 5 which correspond, respectively, to amino acids 99 to 108 and 265 to 281 of SEQ ID NO: 2, are found. The sequences SEQ ID NO: 4 and 5 are, moreover, preceded, respectively, by the amino acids R (position 98 of SEQ ID NO: 2) and K (position 264 of SEQ ID NO: 2) recognized by the trypsin which was used to carry out the proteolysis of purified mannanase and then the sequencing of certain internal peptides (see Example: 2, ♣5).

5. Comparison of the Protein Sequences of Coffee Tree Mannanases.

The alignment (Feng and Doolittle, J. Mol. Evol. 25, 351–360, 1987) of the protein sequence SEQ ID NO: 2, termed mannanase B, with the protein sequence of the endo-β-mannanase termed mannanase A, the complementary DNA of which was previously cloned in the laboratory (Marraccini and Rogers, EP No. 98203742.6), shows that there is less than 56% identity between these two coffee tree proteins (FIG. 1). On the other hand, there are several protein segments which are extremely conserved between these two proteins and that of tomato (Bewley et al., Planta 203, 454–459, 1997) or of other eukaryotic mannanases, such as those of *Aspergillus aculeatus* (Database accession number: L35487) and *Trichoderma reesei* (L25310). Some of these conservations concern, moreover, amino acids presumed to be essential in the activity of the protein, in particular the glutamate (E) residues at position 212, 216, 253 and 333 of the sequence SEQ ID NO: 2, which may be catalytic residues (Bewley et al., 1997). Other amino acid residues, such as the histidine (H) 291, the asparagine (N) 215, the tyrosine (Y) 293 and the tryptophan (W) 377, of the sequence SEQ ID NO: 2 are also conserved and might be essential for the attachment to and the degradation of the substrate.

EXAMPLE 4

Expression of the ManB Coffee Mannanase in E. coli

1. Construction of Expression Plasmids

The manB cDNA sequence corresponding to the sequence SEQ ID NO: 1 was used as template for the amplification of the mature protein sequence (without signal sequence) and without the translational stop codon. The PCR primer B262, corresponding to the sequence SEQ ID NO: 14, primes at the 5' end of the mature manB cDNA and introduces a unique NcoI restriction site encompassing a new ATG initiation codon directly before the mature ManB protein, and primer B260, corresponding to the sequence SEQ ID NO: 15, primes at the 3' end, introducing a SalI restriction site while eliminating the termination codon and producing an in-frame fusion to the HIS-tag sequences provided in plasmid pET24-d (Novagen Inc., 601 Science Drive, Madison Wis., USA) (FIG. 2). Amplification was with the hi-fidelity heat-stable polymerase Pwo (Roche Diagnostics GmbH, GE). One μl of template DNA was mixed with three μl of each oligonucleotide at 100 pmol. $\mu l^{-1}$, 10 μl of 10×Pwo PCR buffer, 6 μl of 2 mM DNTP and 0.5 μl of Pwo polymerase. Amplification was performed in a Perkin-Elmer 9700 PCR machine (Applied Biosystem Division, USA) in 0.2 ml tubes with a 5 min hold at 95° C., followed by 30 cycles of 95° C. for 30 sec, 50° C. for 30 sec and 68° C. for 2 min, and finally held at 4° C.

After PCR, a sample was visualized on a 1% agarose gel to confirm amplification. The amplicon was purified using the Qiagen PCR cleanup kit (Cat. No. 28104, Qiagen INC., USA) and eluted in a 50 μl volume. A 25 μl volume of the purified amplicon was digested with the restriction enzymes NcoI and SalI at 37° C., the product resolved on a 1% agarose gel and the appropriate DNA fragments cut out and eluted using the Qiagen gel extraction kit (Cat. No. 28704). This DNA fragment was ligated into the previously prepared pET24-d vector digested with SalI plus NcoI (dephosphorylated) and transformed into XL1-blue cells (Stratagene, USA). Transformants were selected on LB plates supplemented with 50 μg $ml^{-1}$ kanamycin, analysed by mini plasmid preparations plus restriction enzyme digestions and finally by DNA sequence analysis using the primers 'pET-For', corresponding to the sequence SEQ ID NO: 16 and 'pET-Rev', corresponding to the sequence SEQ ID NO: 17.

The resulting plasmid was named pDP580, the map of which is shown in FIG. 3. Plasmid pDP580 was transformed into the T7 expression host BL21 (DE3) CodonPlus™ RIL (Stratagene, USA) for expression analysis.

2. Induction of Protein Expression

The strain carrying the expression plasmid was grown in LB medium supplemented with the appropriate antibiotics at 37° C. with shaking for 16 h, to provide a fresh starter culture. One ml of the starter was inoculated into 60 ml of LB medium supplemented with the appropriate antibiotics and incubated at 37° C. with shaking until the culture reached an optical density ($O.D._{600}$) of approximately 0.6. IPTG was added to a final concentration of 1 mM and the incubation continued for another 4 h at 37° C. with shaking. A sample of 40 ml was removed and centrifuged at 10 000 rpm and the cell pellet collected (pellet A). The bacterial pellet was suspended in one ml of 50 mM $KPO_4$ pH 7.0, 10 mM imidazole buffer, cooled on ice and sonicated for 30 sec followed by 20 sec at 0° C. The cell debris was pelleted by centrifugation at 12 000 rpm for 30 min (pellet B), the supernatant removed (supernatant B) and both pellet and supernatant stored at −20° C. In order to analyse the proteins by SDS-PAGE, pellet B was solubilized in 50 mM $KPO_4$ pH 7.0, 10 mM imidazole and 8 M urea. Samples were then resolved on 10% Tris-HCl Ready Gels (Bio-Rad Lab., 200 Alfred Nobel Drive, 94547 Hercules Calif. USA, Cat. No. 161–1101) using the recommended conditions.

3. Over-Expression of the E. coli groESL Operon

Recent publications have shown that some over-expressed proteins that are precipitated as inclusion bodies may be recovered in the soluble protein fraction by the co-expression of either the host groESL operon or trigger factor (Vonrhein et al., FEBS Letters 443, 167–169, 1999; Nishihara et al., Appl. Environ Microbiol 33, 884–889, 2000). To test whether the simultaneous over-expression of the E. coli groESL operon could aid the solubilization of the over-expressed coffee endo-β-mannanase enzyme the groESL operon was cloned and expressed in the expression plasmid pKK223-3 (Brosius and Holy, Proc Natl Acad Sci 81, 6929–6933, 1984). Plasmid pKK223-3 (Amersham Pharmacia Biotech, England, Cat. No. 27-4935-01) was chosen because it utilizes the ampicillin resistance gene for selection (no conflict with the other plasmids) and because the expression of the inserted genes is also induced by IPTG, as for pET24-d (Novagen Inc., USA).

Total E. coli chromosomal DNA was PCR-amplified using Pwo polymerase and the primers B452, corresponding to the sequence SEQ ID NO: 18, and B543, corresponding to the sequence SEQ ID NO: 19, as described above.

After PCR a sample was visualized on a 1% agarose gel to confirm amplification. The amplicon was purified using the Qiagen PCR cleanup kit and eluted in a 50 μl volume. A 25 μl volume of the purified amplicon was digested with the restriction enzymes EcoRI and SaiII at 37° C., the product resolved on a 1% agarose gel and the appropriate DNA fragment cut out and eluted using the Qiagen gel extraction kit. The DNA fragment was ligated into the previously prepared pKK223-3 (Amersham Pharmacia Biotech, England) vector digested with SalI plus EcoRI (dephosphorylated) and transformed into XL1-blue cells. Constructs were selected on LB plates supplemented with 100 μg $ml^{-1}$ ampicillin, analysed by mini plasmid preparations plus restriction enzyme digestions, and a positive clone named pDP588 (FIG. 4). Plasmid pDP588 was transformed into the E. coli expression host BL21 (DE3) CodonPlus™ RIL (Stratagene, USA) containing the coffee endo-β-mannanase expression plasmid pDP580 and selected on LB plates supplemented with ampicillin, chloramphenicol and kanamycin. Protein expression was as described above, with the exception that the culture was grown in LB medium supplemented with ampicillin, chloramphenicol and kanamycin at 37° C.

4. Endo-β-Mannanase Assay

Endo-B-mannanase activity was assayed in E. coli cultures prepared and subjected to IPTG-induced expression exactly as described above. Cultures (100 ml) were divided in two when the optical density ($O.D._{600}$) had reached 0.6. Recombinant protein expression was induced with IPTG in one culture (giving IPTG-induced activity), while the other culture was maintained in parallel without induction (control). These 50-ml cultures were then taken to the stages pellet B and supernatant B, as described above.

Activity was assayed in samples from the stages supernatant B and pellet B The sample to be assayed (200 μl of supernatant or pellet B suspended in 200 μl of assay reaction buffer) was added at time zero to 800 μl of reaction buffer (200 mM sodium acetate/acetic acid, 100 mM NaCl, pH 5.0)

containing a suspension of 1% (w/v) insoluble substrate AZCL-galactomannan (Megazyme, Ireland). Reactions were stirred continually at 37° C. Aliquots (200 μl) were taken with time, heated at 100° C. for 5 min and centrifuged at 12 000 g for 5 min, and the supernatant was aliquoted onto a 96-well microplate. Colour was stable following heating. Absorption of the supernatant was read at 595 nm, and activity is expressed as $\Delta 595$ nm.min$^{-1}$.μl sample$^{-1}$. As comparisons are made either between supernatants or between pelleted material, no attempt was made to express specific activity.

5. Expression of the ManB Coffee endo-β-Mannanase Gene

Cultures of the E. coli expression host BL21 (DE3) containing the plasmids CodonPlus RIL (Stratagene, USA) and pDP580, with and without plasmid pDP588, were introduced with IPTG for 4 h, the cells disrupted by sonication and the soluble proteins (supernatant B) and proteins in the cell pellet (pellet B) resolved by SDS-PAGE. The SDS-PAGE of the soluble proteins (supernatant B) (FIG. 5) showed that no strong protein bands corresponding to the predicted size of the coffee endo-β-mannanase construct were present. The SDS-PAGE of the dissolved cell pellet (pellet B), on the other hand, showed the presence of a strong, new protein band for the expression from plasmid pDP580. These results were unchanged when the groESL expression plasmid was included. It was also noted that a construct expressing the full-length endo-β-mannanase gene failed to produce any new protein bands, possibly due to the associated secretion signal sequence.

6. Analysis of Activity of ManB endo-β-Mannanases Expressed in E. coli

The activity of the manB gene recombinant product (ManB endo-β-mannanases) was analysed (Table 1). It can be seen that the endo-β-mannanase expression from pDPS80 is detectable only after induction by IPTG, and only at a low level. This result confirms that the gene designation and enzyme activity correspond. When the E. coli groESL expression plasmid pDP588 is included, the endo-β-mannanase expression increases more than 50 fold, confirming that the co-expression of this chaperone has improved the efficiency of the folding of the endo-β-mannanase protein. However, only very small quantities of the protein remain in soluble form to give detectable enzyme activity, while remaining undetected above the background protein content by SDS-page.

TABLE 1

IPTG-induced endo-β-mannanase activity detected in all E. coli expressing the ManB expression plasmid pDP580, plus with the E. coli groESL expression plasmid pDP588.

| E. coli strain | pDP580 | pDP580 + pDP588 |
|---|---|---|
| Pellet B | | |
| control | 1.6 | 6.6 |
| +IPTG | 2.6 | 142 |
| Supernatant B | | |
| control | 1.0 | 2.8 |
| +IPTG | 1.0 | 74 |

ND = not detected

Activity is expressed as $\Delta 595$ nm.min$^{-1}$;μl sample$^{-1} \times 10^{-5}$
Results represent the average of at least 3 experiments.

EXAMPLE 5

Expression of the ManB Coffee Mannanase in *Yarrowia Lipolytica*

1. Construction of the Expression/Secretion Plasmid

The manB cDNA sequence corresponding to the sequence SEQ ID NO: 1 was used as template for the amplification of the sequence encoding the mature protein (without signal sequence) and without the translational stop codon. PCR primer B281 corresponding to the SEQ ID NO: 20: primes at the 5' end of the mature manB cDNA and introduces a SfiI site allowing directional cloning in frame to a hybrid XPR2-lipase signal sequence present on the *Yarrowia lipolytica* expression/secretion plasmid pNFF296 (FIG. 6). PCR primer B282 corresponding to the SEQ ID NO: 21 primes at the 3' end of the mature manb cDNA and introduces in-frame a 3×HIS sequence just before the stop codon and the SfiI cloning site in front of the lipase terminator of pNFF296. Expression of the inserted gene is under the control of a synthetic XPR2-derived promoter (Mazdak et al., J Mol Microbiol Biotechnol 2, 207–216, 2000). Amplfication was with the high-fidelity heat-stable native Pfu polymerase (Stratagene, USA). One microlitre of template DNA was incubated with 10 mM KCl, 6 mM (NH$_4$)$_2$SO$_4$, 20 mM Tris-HCl, pH 8.0, 0.1% Triton X-100, 2 mM MgCl$_2$, 0.2 mM of each dNTP, 10 μg.ml$^{-1}$ BSA, 0.25 μM of each primer and 3 units of Pfu DNA polymerase (Stratagene, USA) in a Stratagene RoboCycler (Stratagene, USA). PCR was performed as follows: 1 cycle (95° C.—1 min, 50° C.—1 min, 72° C.—3 min), 30 cycles (95° C.—1 min, 50° C.—1 min, 72° C.—3 min) and a final cycle (95° C.—1 min, 50° C.—1 min, 72° C.—10 min). The PCR product was visualized on a 1% agarose gel to confirm amplification, purified using the Qiaquick PCR purification Kit (Cat. No. 28704, Qiagen INC., USA), digested with SfiI and subsequently ligated into the vector pNFF296 (FIG. 6) previously digested with SfiI. This ligation was used to transform E. coli BZ234 (Biozentrum, University of Basel, Klingelbergstr. 50-70CH, 4056 Basel, Switzerland). Constructs were selected on LB plates supplemented with 50 μg.ml$^{-1}$ kanamycin, analysed by mini plasmid preparations plus restriction enzyme digestion and finally by DNA sequence analysis with the manB internal primers B360 and B361 corresponding, respectively, to the sequences SEQ ID NO: 22 and SEQ ID NO: 23, and also with the external primers B358 and B359 corresponding, respectively, to SEQ ID NO: 24 and SEQ ID NO: 25. The resulting plasmid was called pCY316 (FIG. 7).

2. Transformation of *Yarrowia Lipolytica* YLP3

The *Yarrowia lipolytica* host strain YLP3 was derived from the strain polf (MatA ura3-302 leu2-270 xpr2-322 axp-2 SUC2) (Mazdak et al., 2000) by transforming said strain to Leucine prototrophy with a 5.1 kb SalI fragment carrying the *Yarrowia lipolytica* wild-type LEU2 gene and selecting for LEU2 convertants. The *Yarrowia lipolytica* host strain was streaked on a YPD agar plate (1% Difco Bacto Yeast Extract, 2% Difco Bacto Peptone, 2% Glucose, 2% Difco Bacto Agar; Difco-Lee lab., 1475 Athens Hwy, Grayson 30017, GA, USA) and grown overnight at 28° C. 4 ml of liquid YPD, pH 4.0 (1% Difco Bacto Yeast Extract, 1% Difco Bacto Peptone, 1% Glucose, 50 mM Citrate buffer at pH 4.0) were inoculated with freshly grown cells from the YPD plate and grown in a tube on a rotary shaker (200 rpm, 28° C., 8–9 h). An adequate amount of this preculture was used to inoculate 20 ml of YPD, pH 4.0, in a 250 ml Erlenmeyer flask without baffles. This culture was shaken in a rotary shaker at 200 rpm at 28° C. (overnight) until a cell titre of $10^8.ml^{-1}$ had been reached. The cells were centrifuged for 5 min at 3 000 g, washed with 10 ml of sterile water and re-centrifuged. The cellular pellet was suspended in 40 ml of 0.1 M lithium acetate pH 6.0 (adjusted with 10% acetic acid) and shaken in a 250 ml Erlenmeyer at 140 rpm at 28° C. for 60 minutes. The cells were again centrifuged for 5 min at 3 000 g. The cellular pellet was suspended in 2 ml of lithium acetate, pH 6.0, and the competent cells were kept on ice until transformation.

One hundred microlitres of competent cells were mixed with 5-20 µl of plasmid linearized with NotI and 50 µg of carrier DNA (herring sperm DNA sonicated to 100–600 bp, Promega, USA) in a 2 ml tube and incubated for 15 minutes at 28° C. 700 µl of 40% PEG 4000, 0.1 M lithium acetate, pH 6.0, were added and the tubes vigorously shaken at 240 rpm on a rotary shaker at 28° C. for 60 minutes. A 1.2 ml volume of 0.1 M lithium acetate, pH 6.0, was added and mixed, and up to 250 µl were plated on selective agar plates (0.17% Difco Bacto Yeast Nitrogen Base w/o amino acids and ammonium sulphate, 1% glucose, 0.006% L-leucine, 0.1% sodium glutamate, 0.1% Difco Bacto Casamino Acids, 2% agar). The expression plasmid pNFF296 carries a defective URA3 allele which allows the selection of multiple integration of the expression secretion cassette into the YLP3 host strain (Le Dall et al., Current Genetics, 26, 38–44, 1994).

3. Shake-Flask Culturing of *Yarrowia Lipolytica* Transformants

Transformants (Ura$^+$) were re-isolated on selective medium (0.17% Difco Bacto Yeast Nitrogen Base w/o amino acids and ammonium sulphate, 1% glucose, 0.006% L-leucine, 0.1% sodium glutamate, 0.1% Difco Bacto Casamino Acids, 2% agar). A series of clones was grown in shaker-flasks to check for expression and secretion of ManB coffee mannanase into the culture medium:

Small patches of cells were streaked on YPD agar plates and grown overnight at 28° C. The thin layers of cells which had grown were used to inoculate 50 ml of DMI medium in 500 ml Erlenmeyers with 4 lateral baffles. DMI medium contains, per liter: 10 g $KH_2PO_4$; 2.5 g $MgSO_4.7H_2O$; 20 g glucose; 5.1 ml trace element solution; 17 ml vitamin solution; 3 g urea. Urea was dissolved in 15 ml of water and sterile-filtered. The trace element solution contained, per liter; 12.5 g EDTA; 4 g $ZnSO_4.7H_2O$; 6.5 g $MnSO_4.H_2O$; 5 g $CaCl_2.2H_2O$; 30 g $NaH_2PO_4.H_2O$; 2.5 g $FeSO_4.7H_2O$; 0.008 g $H_3BO_3$; 0.0009 g KI; 0.1 g $CuSO_4.5H_2O$; 0.004 g $Na_2MoO_4.2H_2O$; 0.007 g $CoCl_2.6H_2O$; 0.0008 g $NiSO_4.7H_2O$; 0.04 g EDTA, and was sterilized by autoclaving for 20 min at 121° C. The vitamin solution was prepared as previously described (Verduyn et al., Yeast, 8, 501, 1992). The initial pH of the medium was adjusted to 5.0. The cultures were shaken at 140 rpm on a rotary shaker at 28° C. for three days. Aliquots of the cultures were centrifuged at maximum speed (3 000 g) for 15 min and the supernatant was used for the determination of the endo-α-mannanase activity.

4. Endo-β-Mannanase Assay

The culture supernatant (250 µl) was added to 750 µl of reaction buffer (200 mM sodium acetate acetic acid, pH 5.0) containing AZCL-galactomannan (Megazyme, Ireland) to yield a final concentration of 0.5% $_{w/v}$. Samples were incubated at 40° C. with occasional stirring, for 60 minutes. The reactions were stopped by precipitation with 2.5 ml of 95% ethanol.

After centrifugation at maximum speed (3 000 g), the adsorption of the supernatant was read at 590 nm. Endo-β-mannanase activity is expressed as $\Delta595$ $nm.hr^{-1}.ml$ supernatant$^{-1}$. A blank (250 µl of reaction buffer) and a culture supernatant of a YLP3 transformant carrying an empty plasmid (pNFF296) were included in parallel as controls. A total of 21 transformants were screened for endo-β-mannanase activity. All transformants transformed with the plasmid pCY316 showed various levels of enzyme activity, while no activity could be detected in the control transformant carrying the empty plasmid pNFF296. For six independent pCY316 transformants, the experiment was repeated twice and the results of the activity assays are shown in Table 2.

TABLE 2

Endo-B-mannanase activity detected in culture supernatants of different independent clones of *Yarrowia lipolytica* transformed with the vector pCY316.

| Transformants | Activity[*] |
| --- | --- |
| YLP3 (pCY316) # 1 | 0.268 |
| YLP3 (pCY316) # 4 | 0.328 |
| YLP3 (pCY316) # 11 | 0.246 |
| YLP3 (cPY316) # 13 | 0.288 |
| YLP3 (cPY316) # 16 | 0.320 |
| YLP3 (pCY316) # 21 | 0.271 |
| YLP3 (pNFF296) # 1 (empty plasmid) | 0 |

[*]Activity is expressed as $\Delta590$ $nm.hr^{-1}.250$ µl supernatant$^{-1}$. Background values of the blank [buffer] have already been deducted from the final values given above.
# : indicates the numbering of the transformed clones. Results represent the average of 3 experiments.

What is claimed is:

1. A fragment of isolated DNA from coffee encoding at least one endo-β-mannanase enzyme, which comprises the nucleic acid sequence SEQ ID NO:1 or comprises at least one of the following sequences: SEQ ID NO: 2, SEQ ID NO: 3, SEQ ID NO: 4 or SEQ ID NO: 5, wherein the fragment of DNA encodes at least one endo-β-mannanase enzyme.

2. A fragment of DNA according to claim 1, comprising at least nucleotides 62 to 1312 of the nucleic acid sequence SEQ ID NO.: 1.

3. A recombinant vector comprising the fragment of DNA according to claim 1.

4. A recombinant vector comprising the fragment of DNA according to claim 2.

5. A transformed plant cell comprising the fragment of DNA according to claim 1, wherein said fragment is integrated into the plant cell genome.

6. The plant cell according to claim 5, which is a coffee cell.

7. A transformed plant cell comprising the fragment of DNA according to claim 2, wherein said fragment is integrated into the plant cell genome.

8. The plant cell according to claim 7, which is a coffee cell.

9. A plant or seed comprising transformed plant cells according to claim 5.

10. A plant or seed comprising transformed plant cells according to claim 7.

* * * * *